United States Patent
Miller

(10) Patent No.: US 7,037,111 B2
(45) Date of Patent: *May 2, 2006

(54) MODIFIED TOOTH POSITIONING APPLIANCES AND METHODS AND SYSTEMS FOR THEIR MANUFACTURE

(75) Inventor: Ross J. Miller, Sunnyvale, CA (US)

(73) Assignee: Align Technology, Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/199,947

(22) Filed: Jul. 18, 2002

(65) Prior Publication Data

US 2004/0191728 A1 Sep. 30, 2004

Related U.S. Application Data

(63) Continuation of application No. 09/658,340, filed on Sep. 8, 2000, now Pat. No. 6,497,574.

(51) Int. Cl.
*A61C 11/00* (2006.01)
*G09B 23/28* (2006.01)

(52) U.S. Cl. ..................... 433/213; 434/263

(58) Field of Classification Search ............... 433/213, 433/214, 74, 34, 24

See application file for complete search history.

(56) References Cited

U.S. PATENT DOCUMENTS

| | | |
|---|---|---|
| 2,467,432 A | 4/1949 | Kesling |
| 3,660,900 A | 5/1972 | Andrews |
| 3,860,803 A | 1/1975 | Levine |
| 3,916,526 A | 11/1975 | Schudy |

(Continued)

FOREIGN PATENT DOCUMENTS

DE 3900168 * 10/1989 ............... 433/213

(Continued)

OTHER PUBLICATIONS

Alexander et al., "The DigiGraph Work Station Part 2, Clinical Management," *JCO* (Jul. 1990), pp. 402-407

(Continued)

*Primary Examiner*—Cary E. O'Connor
(74) *Attorney, Agent, or Firm*—Townsend and Townsend and Crew LLP

(57) ABSTRACT

The present invention provides improved devices, systems and methods for producing dental molds, each having portions representing a patient's oral soft tissue and a desired tooth configuration. These molds are designed for use in the fabrication of appliances used in orthodontic treatment, particularly, elastic repositioning appliances. However, they may also be used in the fabrication of traditional appliances, such as retainers and positioners, used, for example in the final or finishing stages of an otherwise conventional treatment. The dental molds are comprised of a mold or relief of the patient's soft tissue, such as a palate, facial gingival tissue and/or lingual gingival tissue, and a separate or separable mold or relief of the patient's dental arch having teeth in a desired tooth configuration. Since, the tooth configuration will change as a patient progresses through orthodontic treatment, the relief of the dental arch will be fabricated separately from the relief of the oral soft tissue. Typically, the dental arch relief will be fabricated using rapid prototyping methods. The soft tissue relief may also be fabricated using rapid prototyping, however it may also be fabricated using traditional mold making methods, i.e., casting with plaster or other mold making materials. In either case, the resulting dental mold with be comprised of a "split-mold" having fixedly or removably joined arch and soft tissue reliefs.

12 Claims, 5 Drawing Sheets

U.S. PATENT DOCUMENTS

| | | | |
|---|---|---|---|
| 3,949,478 | A * | 4/1976 | Schinhammer ............... 433/3 |
| 3,950,851 | A | 4/1976 | Bergersen |
| 4,014,096 | A | 3/1977 | Dellinger |
| 4,099,329 | A * | 7/1978 | Hawthorne ............... 433/34 |
| 4,195,046 | A | 3/1980 | Kesling |
| 4,324,546 | A | 4/1982 | Heitlinger et al. |
| 4,348,178 | A | 9/1982 | Kurz |
| 4,478,580 | A | 10/1984 | Barrut |
| 4,504,225 | A | 3/1985 | Yoshii |
| 4,505,673 | A | 3/1985 | Yoshii |
| 4,575,805 | A | 3/1986 | Moermann et al. |
| 4,611,288 | A | 9/1986 | Duret et al. |
| 4,656,860 | A | 4/1987 | Orthuber et al. |
| 4,663,720 | A | 5/1987 | Duret et al. |
| 4,742,464 | A | 5/1988 | Duret et al. |
| 4,755,139 | A | 7/1988 | Abbatte et al. |
| 4,763,791 | A | 8/1988 | Halverson et al. |
| 4,767,330 | A * | 8/1988 | Burger ............... 433/213 |
| 4,793,803 | A | 12/1988 | Martz |
| 4,798,534 | A | 1/1989 | Breads |
| 4,837,732 | A | 6/1989 | Brandestini et al. |
| 4,850,864 | A | 7/1989 | Diamond |
| 4,856,991 | A | 8/1989 | Breads et al. |
| 4,936,862 | A | 6/1990 | Walker et al. |
| 4,937,928 | A | 7/1990 | van der Zel |
| 4,964,770 | A | 10/1990 | Steinbichler et al. |
| 4,975,052 | A | 12/1990 | Spencer et al. |
| 5,011,405 | A | 4/1991 | Lemchen |
| 5,017,133 | A | 5/1991 | Miura |
| 5,027,281 | A | 6/1991 | Rekow et al. |
| 5,035,613 | A | 7/1991 | Breads et al. |
| 5,055,039 | A | 10/1991 | Abbatte et al. |
| 5,059,118 | A | 10/1991 | Breads et al. |
| 5,100,316 | A | 3/1992 | Wildman |
| 5,120,229 | A * | 6/1992 | Moore et al. ............... 434/263 |
| 5,121,333 | A | 6/1992 | Riley et al. |
| 5,128,870 | A | 7/1992 | Erdman et al. |
| 5,131,843 | A | 7/1992 | Hilgers et al. |
| 5,131,844 | A | 7/1992 | Marinaccio et al. |
| 5,139,419 | A | 8/1992 | Andreiko et al. |
| 5,184,306 | A | 2/1993 | Erdman et al. |
| 5,186,623 | A | 2/1993 | Breads et al. |
| 5,257,203 | A | 10/1993 | Riley et al. |
| 5,273,429 | A | 12/1993 | Rekow et al. |
| 5,278,756 | A | 1/1994 | Lemchen et al. |
| 5,338,198 | A | 8/1994 | Wu et al. |
| 5,340,309 | A | 8/1994 | Robertson |
| 5,342,202 | A | 8/1994 | Deshayes |
| 5,368,478 | A | 11/1994 | Andreiko et al. |
| 5,382,164 | A | 1/1995 | Stern |
| 5,395,238 | A | 3/1995 | Andreiko et al. |
| 5,431,562 | A | 7/1995 | Andreiko et al. |
| 5,440,496 | A | 8/1995 | Andersson et al. |
| 5,447,432 | A | 9/1995 | Andreiko et al. |
| 5,452,219 | A | 9/1995 | Dehoff et al. |
| 5,454,717 | A | 10/1995 | Andreiko et al. |
| 5,456,600 | A | 10/1995 | Andreiko et al. |
| 5,474,448 | A | 12/1995 | Andreiko et al. |
| 5,518,397 | A | 5/1996 | Andreiko et al. |
| 5,533,895 | A | 7/1996 | Andreiko et al. |
| 5,542,842 | A | 8/1996 | Andreiko et al. |
| 5,549,476 | A | 8/1996 | Stern |
| 5,587,912 | A | 12/1996 | Andersson et al. |
| 5,605,459 | A | 2/1997 | Kuroda et al. |
| 5,607,305 | A | 3/1997 | Andersson et al. |
| 5,645,421 | A | 7/1997 | Slootsky |
| 5,655,653 | A | 8/1997 | Chester |
| 5,683,243 | A | 11/1997 | Andreiko et al. |
| 5,733,126 | A | 3/1998 | Andersson et al. |
| 5,740,267 | A | 4/1998 | Echerer et al. |
| 5,975,893 | A | 11/1999 | Chishti et al. |
| 6,227,851 | B1 * | 5/2001 | Chishti et al. ............... 433/24 |
| 6,524,105 | B1 * | 2/2003 | Raffeiner ............... 433/213 |

FOREIGN PATENT DOCUMENTS

| | | |
|---|---|---|
| EP | 091876 A1 | 10/1983 |
| EP | 299490 A2 | 1/1989 |
| EP | 376873 A2 | 7/1990 |
| EP | 490848 B1 | 6/1992 |
| EP | 774933 B1 | 5/1997 |
| EP | 541500 A1 | 6/1998 |
| EP | 731673 B1 | 9/1998 |
| FR | 2369828 A1 | 6/1978 |
| FR | 2652256 A1 | 3/1991 |
| WO | WO 90/08512 A1 | 8/1990 |
| WO | WO 91/04713 A1 | 4/1991 |
| WO | WO 94/10935 A1 | 5/1994 |
| WO | WO 98/44865 A1 | 10/1998 |
| WO | WO 98/58596 A1 | 12/1998 |

OTHER PUBLICATIONS

Altschuler et al., "Laser Electro-Optic System for Rapid Three-Dimensional (3D) Topographic Mapping of Surfaces," *Optical Engineering*, vol. 20(6) (1981), pp. 953-961.

Altschuler et al., "Measuring Surfaces Space-Coded by a Laser-Projected Dot Matrix," *SPIE Imaging Applications for Automated Industrial Inspection and Assembly*, vol. 182 (1979), p. 187-191.

Altschuler et al., "Analysis of 3-D Data for Comparative 3-D Serial Growth Pattern Studies of Oral-Facial Structures," Program and Abstracts of Papers, Feb. 1975, *Journal of Dental Research*, vol. 54, IADR Abstracts 1979, 2 pages total.

Altschuler, "3D Mapping of Maxillo-Facial Prosthesis," AADR Abstract #607, 1980, 2 pages total..

American Association for Dental Research, Summary of Activities, Mar. 20-23, 1980, Los Angeles, CA, p. 195.

Andersson et al., "Clinical Results with Titanium Crowns Fabricated with Machine Duplication and Spark Erosion," *Acta Odontological Scandinavia*, vol. 47 (1989), pp. 279-286.

Baumrind et al., "A stereophotogrammetric system for the detection of prosthesis loosening in total hip arthroplasty, Applications of Human Biostereometrics (NATO)," Proceedings of the Society of Photo-Optical Instrumentation Engineers, vol. 166, Jul. 9-13, 1978, pp. 112-123.

Baumrind et al., Mapping the Skull in 3-D, Reprinted from The Journal, *California Dental Association*, vol. 48, No. 2 (1972 Fall Issue) 11 pages total.

Baumrind et al., "Seminars in Orthodontics," *Seminars in Orthodontics*, vol. 7, No. 4 (Dec. 2001), p. 222.

Baumrind, "A System for Craniofacial Mapping Through the Integration of Data from Stereo X-Ray Films and Stereo Photographs," An invited paper submitted to the 1975 American Society of Photogram. Symposium on Close-Range Photogram. Systems, University of Ill., Aug. 26-30, 1975, pp. 1-25.

Baumrind, "Integrated Three-Dimensional Craniofacial Mapping: Background, Principles, and Perspectives," *Seminars in Orthodontics*, vol. 7, No. 4 (Dec. 2001), pp. 223-232.

Begole et al., "A Computer System for the Analysis of Dental Casts," *The Angle Orthodontist*, vol. 51 No. 3 (Jul. 1981), pp. 253-259.

Bernard et al., "Computerized diagnosis in Orthodontics for Epidemiological Studies" (progress report), Abstracts of Papers, *Journal of Dental Research*; vol. 71, Special Issue Mar. 1-14, 1992, pp. 28-36.

Bhatia et al., "A Computer-Aided Design for Orthognathic Surgery," *British Journal of Oral and Maxillofacial Surgery*, vol. 22 (1984), pp. 237-253.

Biggerstaff et al., "Computerized analysis of occlusion in the postcanine dentition," *American Journal of Orthodontics*, vol. 61, No. 3 (Mar. 1972), pp. 245-254.

Biggerstaff, "Computerized Diagnostic Setups and Simulations," *The Angle Orthodontist*, vol. 40, No. 1 (Jan. 1970), pp. 28-36.

Brandestini et al., "Computer Machined Ceramic Inlays: In Vitro Marginal Adaptation," *Journal of Dental Research*, vol. 64/Special Issue/Abstracts, IADR/AADR Abstracts 1985, 1 page total.

Brook et al., An Image Analysis System for the Determination of Tooth Dimensions from Study Casts: Comparison with Manual Measurements of Mesio-distal Diameter, Abstract of Papers, 1985, Dept. of Children's Dentistry and Orthodontics, *J Dent Res.*, Mar. 1986, pp. 428-431.

Burstone (interview), "Dr. Charles J. Burstone on The Uses of the Computer in Orthodontic Practice (Parts1 and 2)," *Journal of Clinical Orthodontics*, (Part 1) vol. 8, No. 7 , Jul. 1979; (Part 2) vol. 8, No. 8 pp. 539-551, Aug. 1979.

Burstone et al., "Precision adjustment of the transpalatal lingual arch: Computer arch form predetermination," *Am. Journal of Orthodontics*, vol. 79, No. 2 (Feb. 1981), pp. 115-133.

Chaconas et al., "The DigiGraph Work Station, Part 1, Basic Concepts," *JCO* (Jun. 1990), pp. 360-367.

Chafetz et al., "Subsidence of the Femoral Prosthesis, A Stereophotogrammetric Evaluation," *Clinical Orthopaedics and Related Research*, No. 201 (Dec. 1985), pp. 60-67.

Chiappone, "Constructing the gnathologic setup and positioner" *J. Clin. Orthod.*, 14:121-133, 1980.

Cottingham, "Gnathologic clear plastic positioner" *Am. J. Orthod.*, 55:23-31, 1969.

Crawford, "Computers in Dentistry: Part 1: CAD/CAM: The Computer Moves Chairside," "Part 2: F. Duret—A Man With A Vision," "Part 3: The Computer Gives New Vision-Literally," "Part 4: Bytes 'N Bites" The Computer Moves From The Front Desk To The Operatory, *Canadian Dental Journal*, vol. 54(9), , (1988), pp. 661-666.

Crawford, "CAD/CAM in the Dental Office: Does It Work?" *Canadian Dental Journal*, vol. 57, No. 2 (Feb. 1991), pp. 121-123.

Crooks, "CAD/CAM Comes to USC," *USC Dentistry*, (Spring 1990) pp. 14-17.

Cureton, "Correcting malaligned mandibular incisors with removable retainers" *J. Clin. Orthod.*, 30:390-395, 1996.

Curry et al., "Integrated Three-Dimensional Craniofacial Mapping at the Craniofacial Research Instrumentation Laboratory/University of the Pacific," *Seminars in Orthodontics*, vol. 7, No. 4 (Dec. 2001), pp. 258-265.

Cutting et al., "Three-Dimensional Computer-Assisted Design of Craniofacial Surgical Procedures: Optimization and Interaction with Cephalometric and CT-Based Models," *Plastic and Reconstructive Surgery*, vol. 77, No. 6 (Jun. 1986), pp. 877-885.

DCS Dental AG, "The CAD/CAM 'DCS Titan System' for Production of Crowns/Bridges" *DSC Production AG*, Jan. 1992, pp. 1-7.

Defranco et al., "Three-Dimensional Large Displacement Analysis of Orthodontic Appliances," *J. Biomechanics*, vol. 9 (1976), pp. 793-801.

Dental Institute University of Zurich Switzerland, Program for International Symposium on Computer Restorations: State of the Art of the CEREC-Method, May 1991, 3 pages total.

DenTrac Corporation, Dentrac document, pp. 4-13.

Duret et al, "CAD-CAM in Dentistry," *Journal of the American Dental Association*, vol. 117 (Nov. 1988), pp. 715-720.

Duret et al., "CAD/CAM imaging in dentistry," *Current Opinion in Dentistry*, vol. 1 (1991), pp. 150-154.

Duret, "The Dental CAD/CAM, General Description of the Project," *Hennson International Product Brochure*, Jan. 1986., 18 pages total.

Duret, "Vers une prosthese informatisee," (English translation also attached), *Tonus*, vol. 75, (Nov. 15, 1985). pp. 55-57.

Economides, "The Microcomputer in the Orthodontic Office," *JCO*, (Nov. 1979), pp. 767-772.

Elsasser, "Some observations on the history and uses of the Kesling positioner" *Am. J. Orthod.*, 36:368-374, 1950.

Faber et al.,"Computerized interactive orthodontic treatment planning," *Am. J. Orthod.*, vol. 73, No. 1 (Jan. 1978), pp. 36-46.

Felton et al. "A computerized analysis of the shape and stability of mandibular arch form," *Am. Journal of Orthodontics and Dentofacial Orthopedics*, vol. 92, No. 6 (Dec. 1987), pp. 478-483.

Friede et al., Accuracy of Cephalometric Prediction in Orthognathic Surgery, Abstract of Papers, *Journal of Dental Research*, vol. 70 (1987), pp. 754-760.

Gim-Alldent Deutschland, "Das DUX System: Die Technik" 4 pages total.

Grayson, "New Methods for Three Dimensional Analysis of Craniofacial Deformity," Symposium: Computerized Facial Imaging in Oral and Maxilofacial Surgery, AAOMS Sep. 13, 1990, 3 pages total.

Guess et al., Computer Treatment Estimates in Orthodontics and Orthognathic Surgery, *JCO*, (Apr., 1989), pp. 262-228.

Heaven et al., "Computer-based Image Analysis of Artificial Root Surface Caries," "Automated Identification of Landmarks in Cephalometric Radiographs," Abstracts of Papers, *Journal of Dental Research*, vol. 67, Mar. 9-13, 1988, 2 pages total.

Hoffmann et al., "Role of Cephalometry for Planning of Jaw Orthopedics and Jaw Surgery Procedures," (Article Summary in English, article in German), *Informationen*, (Mar. 1991), pp. 375-396.

Huckins, "CAD-CAM Generated Mandibular Model Prototype from MRI Data," *AAOMS* 1999, p. 96.

Inside the ADA, *Journal Of The American Dental Assoc.*, vol. 118 (Mar. 1989) 9 pages total.

JCO Interviews, "Craig Andreiko , DDS, MS on the Elan and Orthos Systems", JCO, (Aug. 1994), pp. 459-468.

JCO Interviews, "Dr. Homer W. Phillips on Computers in Orthodontic Practice, Part 2," JCO, (Dec. 1983), pp. 819-831.

Jerrold, "The problem, electronic data transmission and the law," *AJO-DO*, (Apr. 1988), pp. 478-479.

Jones et al., "An Assessment of the Fit of a Parabolic Curve to Pre- and Post-Treatment Dental Arches," *British Journal of Orthodontics*, vol. 16 (1989), pp. 85-93.

Kamada et al., "Case reports on tooth positioners using LTV vinyl silicone rubber" J. Nihon University School of Dentistry, 26(1):11-29, 1984.

Kamada et al., "Construction of tooth positioners with LTV vinyl silicone rubber and some case reports" J. Nihon University School of Dentistry, 24(1):1-27, 1982.

Kanazawa et al., "Three-Dimensional Measurements of the Occlusal Surfaces of Upper Molars in a Dutch Population," *J. Dent. Res.*, vol. 63, No. 11 (Nov. 1984), pp. 1298-1301.

Kesling, "Coordinating the predetermined pattern and tooth positioner with conventional treatment" *Am. J. Orthod. Oral. Surg.*, 32:285-293, 1946.

Kesling, "The philosophy of the tooth positioning appliance" *Am. J. Orthod. Oral. Surg.*, 31(6):297-304, 1945.

Kleemann et al., "The speed positioner" *J. Clin. Orthod.*, 30:673-680, 1996.

Kuroda et al., "Three-dimensional dental cast analyzing system using laser scanning" *Am. J. Orthod. Dentofac. Orthop.*, 110:365-369, 1996.

Laurendeau et al., "A Computer-Vision Technique for the Acquisition and Processing of 3-D Profiles of Dental Imprints: An Application in Orthodontics," *IEEE Transactions on Medical Imaging*, vol. 10, No. 3 (Sep. 1991), pp. 453-461.

Leinfelder et al., "A new method for generating ceramic restorations: a CAD-CAM system," *Journal Of The American Dental Assoc.*, vol. 118, No. 6 (Jun. 1989), pp. 703-707.

Mcnamara et al., *Orthodontic and Orthopedic Treatment in the Mixed Dentition*, Neeham Press, Jan. 1993, pp. 347-353.

Mcnamara et al., "Invisible Retainers", *J. Clinical Orthodontics*, (Aug. 1965) pp. 570-578.

Moermann et al., "Computer Machined Adhesive Porcelain Inlays: Margin Adaptation after Fatigue Stress," IADR Abstract 339, *Journal of Dental Research*, vol. 66(a) (1987), p. 339.

Mörmann et al., "Marginal Adaptation von adhasiven Porzellaninlays in vitro, "*Schwizerische Monatsschrift fur Zahnmedizin*, vol. 85 (1985), p. 1118-1129.

Mörmann et al., "Marginale Adaptation von adhäsuven Porzellaninlays in vitro," Separatdruck aus: Schweiz. Mschr. Zahnmed. 95: 1118, 1985.

Nahoum, "The vacuum formed dental contour appliance" *The New York State Dental Journal*, 30(9):385-390, Nov. 1964.

Nash, "CEREC CAD/CAM Inlays: Aesthetics and Durability in a Single Appointment," *Dentistry Today*, (Oct. 1990), pp. 20, 22-23, 54.

Nishiyama et al., "A new construction of tooth repositioner by LTV vinyl silicone rubber" J. Nihon University School of Dentistry, 19(2):93-102, 1977.

Pinkham, "'Foolish' Concept Propels Technology," *Dentist*, Jan./Feb. 1989, 3 pages total.

Pinkham, "Inventor's CAD/CAM may transform dentistry," *Dentist*, Sep. 1990, 3 pages total.

Ponitz, Invisible Retainers, 59 *Am. J. Orthodontics*, Mar. 1971, pp. 266-272.

Procera Research Projects, PROCERA Research Projects 1993—Abstract Collection, 1993, pp. 3-28.

Rekow, "A Review of the Developments in Dental CAD/CAM Systems,"(contains references to Japanese efforts and content of the papers of particular interest to the clinician are indicated with a one-line summary of their content in the bibliography), Dental Clinics: *Prosthodontics and Endodontics*, pp. 25-33, 1992.

Rekow, "CAD/CAM in Dentistry: A Historical Perspective and View of the Future," *Journal*, vol. 58 No. 4, (Apr. 1992), pp. 283, 287-288.

Rekow, "Computer-Aided Design and Manufacturing in Dentistry: A Review of the State of the Art," *The Journal of Prosthetic Dentistry*, vol. 58. No. 4 (Oct. 1987). pp. 512-516.

Rekow, "Dental CAD-CAM Systems: What is the State of the Art?" *Journal of the American Dental Assoc.*, vol. 122 (1991), pp. 43-48.

Rekow, "Feasibility of an Automated System for Production of Dental Restorations," PhD Thesis, Univ. of Minnesota, Nov. 1988, 244 pages total.

Richmond et al., Research Reports, "The development of a 3D Cast Analysis System," *British Journal of Orthodontics*, pp. 53-54.

Richmond, "Recording the dental cast in three dimensions," *Am. J. Orthod. Dentofac. Orthop.*, vol. 92, No. 3, (Sep. 1987), pp. 199-206.

Rudge, "Dental arch analysis: arch form, A review of the literature," *European Journal of Orthodontics*, vol. 3, No. 4 (1981), pp. 279-284.

Sakuda et al., "Integrated information-processing system in clinical orthodontics: An approach with use of a computer network system," *Am. J. Orthod. Dentofac. Orthop.* vol. 101 No. 3 (Mar. 1992), pp. 210-220.

Schellhas et al., "Three-Dimensional Computer Tomography in Maxillofacial Surgical Planning," *Arch Otolamgol Head Neck Surg.* vol. 114 (Apr. 1988), pp. 438-442.

Segu et al., "Computer-aided Cefalometry and New Mechanics in Orthodontics" (Article Summary in English, article in German), *Fortschr. Kieferorthop.* 44, 370-376 (Nr. 5), 1983.

Shilliday, "Minimizing finishing problems with the mini-positioner" *Am. J. Orthod.* 59:596-599, 1971.

Siemens, "CEREC—Computer-Reconstruction, "High Tech in der Zahnmedizin, 14 page total.

Sirona Dental Systems GmbH, CEREC 3D, Manuel utilisateur, Version 2.0X (in French), 2003, 114 pages total.

Stoll et al., "Computer-aided Technologies in Dentistry" (Article Summary in English, article in German). *Dtsch Zahnärztl Z* 45, 314-322, 1990.

U.S. Department of Commerce, National Technical Information Service, "Automated Crown Replication Using Solid Photography SM," Solid Photography Inc. Melville NY, Oct. 1977, 21 pages total.

U.S. Department of Commerce, National Technical Information Service, "Holodontography: An Introduction to Dental Laser Holography," School of Aerospace Medicine Brooks AFB Tex, Mar. 1973, 37 pages total.

U.S. Appl. No. 60/050,342, filed Jun. 20, 1997, 41 pages total.

Van Der Linden et al., Three-Dimensional Analysis of Dental Casts by Means of the Optocom, *J Dent Res*, Jul.-Aug. 1972, p. 1101.

Van Der Linden, "A New Method to Determine Tooth Positions and Dental Arch Dimensions," Jul.-Aug. 1972, p. 1104.

Van der zel, "Ceramic-fused-to-metal Restorations with a New CAD/CAM System," *Quintessence International*, vol. 24(11) (1993), pp. 769-778.

Varady et al., "Reverse Engineering of Geometric Models—An Introduction," May 13, 1996, pp. 1-28.

Warunek et al., "Clinical use of silicone elastomer appliances" *JCO*, MH (10):694-700, 1989.

Warunek et al., "Physical and mechanical properties of elastomers in orthodontic positioners" *Am. J. Orthod. Dentofac. Orthop.*, 95:388-400, 1989.

Wells, "Application of the positioner appliance in orthodontic treatment" *Am. J. Orthodont.*, 58:351-366, 1970.

Williams, Dentistry and CAD/CAM: Another French Revolution, *Journal of Dental Practice Admin.*, Jan./Mar. 1987, pp. 2-5.

Williams, "The Switzerland and Minnesota Developments in CAD/CAM," *Journal of Dental Practice Admin.*, pp. 50-55, Apr./Jun. 1987.

Wishan, New Advances in Personal Computer Applications for Cephalometric Analysis, Growth Prediction, Surgical Treatment Planning and Imaging Processing, Symposium: Computerized Facial Imaging in Oral and Maxilofacial Surgery, AAOMS, Sep. 13, 1990, p. 5.

Yamamoto et al., "Three-Dimensional Measurement of Dental Cast Profiles and Its Applications to Orthodontics," Annual Int'l Conf. of IEEE Engineering in Medicine and Biology Society, vol. 12, No. 5, pp. 2051-2053, 1990.

Yamamoto et al., "Optical measurement of dental cast profile and application to analysis of three-dimensional tooth movement in orthodontics," *Frontiers in Med. and Biol. Eng'g*, vol. 1, No. 2 (1988), pp. 119-130.

* cited by examiner

MODIFIED TOOTH POSITIONING APPLIANCES AND METHODS AND SYSTEMS FOR THEIR MANUFACTURE

CROSS-REFERENCES TO RELATED APPLICATIONS

This application is a continuation application which claims priority to U.S. application Ser. No. 09/658340 filed on Sep. 8, 2000, now U.S. Pat. No. 6,497,574, the full disclosure of which is incorporated herein by reference.

STATEMENT AS TO RIGHTS TO INVENTIONS MADE UNDER FEDERALLY SPONSORED RESEARCH OR DEVELOPMENT

Not Applicable

REFERENCE TO A "SEQUENCE LISTING," A TABLE, OR A COMPUTER PROGRAM LISTING APPENDIX SUBMITTED ON A COMPACT DISK

Not Applicable

BACKGROUND OF THE INVENTION

The present invention is related generally to the field of orthodontics. Particularly, the present invention is related to methods, systems and devices involving split dental molds. More particularly, the present invention involves dental molds having tooth portions and oral soft tissue portions of different types.

Traditional methods of dental mold making are well known, such as those described in Graber, *Orthodontics: Principle and Practice*, Second Edition, Saunders, Philadelphia, 1969, pp. 401–415. Typically, these methods involve forming an impression of the patent's dentition using a suitable impression material, such as alginate or polyvinylsiloxane (PVS). Impressions of the upper jaw typically include the teeth, the palate and gingival tissue surrounding the teeth on the facial and lingual surfaces. Impressions of the lower jaw typically include the teeth and gingival tissue surrounding the teeth on the facial and lingual surfaces. Plaster is then poured into the impression to form a relief of the dental features. The relief is a permanent, three-dimensional mold of the dentition and oral tissues.

Improved methods of mold making include rapid prototyping. Rapid prototyping is a technology which has developed in the last decade. Through the use of modern solid modeling CAD packages, combined with laser systems and new materials, solid parts may now be generated directly from a computer model. Examples of this technology include stereolithography (SLA), laminate object manufacturing (LOM), and fused deposition modeling (FDM), to name a few.

Stereolithography is a method that employs an ultraviolet laser to cure a thin layer of liquid plastic into a solid. The process operates by taking a thin layer of the light-sensitive liquid plastic and passing the laser beam over the points where the part is solid. Once a pass is completed, another layer of the liquid is added to the existing part, and the process repeats until the full part height is achieved. SLA parts are extremely accurate, and tend to have excellent surface finishes. A variety of SLA materials are available for different purposes, including waxes, plastics, and flexible elastomers.

Laminate object manufacturing builds a part by taking individual sheets of paper that have a layer of glue on one side and building up successive sections of a part. As each layer is laid down, a laser beam passes over the edges of the part, detailing the part and separating the part from the excess material. In addition, the laser beam creates a grid throughout the excess material. After the final sheet is laid down, the part may be separated from the excess material by removing cubes of the grid in a systematic fashion. LOM parts are accurate, and very easy to sand and paint. LOM parts also have different strengths in different directions due to the paper layers.

Fused deposition modeling is a process that most closely resembles a miniature glue gun. In fused deposition modeling, a heat softening and curing plastic is melted in a small nozzle which puts down a very fine bead wherever the solid part is supposed to be. FDM parts have a rougher surface finish than an SLA part, but typically are stronger and more durable. In all cases, parts created by rapid prototyping methods are generated relatively quickly and are accurate to a few thousandths of an inch.

Producing a dental mold with rapid prototyping methods requires the use of a computerized model or digital data set representing the dental geometry and tooth configuration. The model is used to guide the mold making process to produce a replica or relief of the computerized model. The resulting relief is a three-dimensional mold of the dentition. This method of making dental molds is particularly applicable to situations in which multiple molds are needed to be produced. In this case, one computerized model may be used to make a number of molds in an automated fashion. In addition, this method is applicable to situations in which a mold of a tooth arrangement which differs from the patient's current tooth arrangement is needed to be produced or molds of multiple tooth arrangements which differ from each other and the patient need to be produced. In either case, the computerized model of the patient's teeth may be manipulated to portray each new tooth arrangement and a mold may be produced to reflect each successive arrangement. This may be repeated any number of times to derive a number of molds with differing tooth arrangements. Such techniques may speed production time and reduce costs by eliminating the need for repeated casting and artistic resetting of teeth in traditional mold manufacturing.

Series of dental molds, such as those described above, may be used in the generation of elastic repositioning appliances for a new type of orthodontic treatment being developed by Align Technology, Inc., Santa Clara, Calif., assignee of the present application. Such appliances are generated by thermoforming a thin sheet of elastic material over a mold of a desired tooth arrangement to form a shell. The shell of the desired tooth arrangement generally conforms to a patient's teeth but is slightly out of alignment with the initial tooth configuration. Placement of the elastic positioner over the teeth applies controlled forces in specific locations to gradually move the teeth into the desired configuration. Repetition of this process with successive appliances comprising new configurations eventually moves the teeth through a series of intermediate configurations to a final desired configuration. A full description of an exemplary elastic polymeric positioning appliance is described in U.S. Pat. No. 5,975,893, and in published PCT application WO 98/58596 which designates the United States and which is assigned to the assignee of the present invention. Both documents are incorporated by reference for all purposes.

To carry out such orthodontic treatment, a series of computer models or digital data sets will be generated, stored and utilized to fabricate a series of representative dental molds. Typically, only the digital information related to the tooth arrangement will be stored due to cost and space limitations. However, to form a properly fitting elastic repositioning appliance or other dental appliance, it will at times be necessary to include in the mold a patient's oral soft tissue, such as a palate, facial gingival tissue and/or lingual gingiva tissue. This may be the case when adding accessories to a basic elastic repositioning shell, such as palatal bars, lingual flanges, lingual pads, buccal shields, buccinator bows or wire shields, a full description of which is described in U.S. Provisional Patent Application No. 60/199649 filed Apr. 25, 2000, and the full disclosure is hereby incorporated by reference for all purposes. These accessories may contact or interact with portions of the soft tissue requiring a mold of such tissues to properly position the accessory in or on the appliance. In addition, this may be the case when producing traditional orthodontic retainers and positioners. Traditional appliances may be used as part of an orthodontic treatment plan utilizing elastic repositioning appliances, particularly in the final stages of treatment. During such stages, for example, any residual intrusion of the teeth due to the presence of elastic appliances may be corrected with the use of a traditional retainer. Such retainers typically comprise a polymeric replica of the palate or portions of the gingiva which support metal wires which wrap around the perimeter of the teeth.

Generating dental molds including both the tooth arrangement and the geometry of the oral soft tissue of a patient for each stage of treatment throughout orthodontic treatment is, however, expensive, due to cost of materials, fabrication time and space required for storage of digital information. Likewise, generating such a mold during treatment as necessary is also expensive due to 1) the added space required to store the additional digital information of the oral soft tissue, and 2) the time and labor required to manipulate the digital information to join a given tooth arrangement with an oral soft tissue geometry each time a mold is desired to be produced.

Therefore, improved devices, systems and methods are desired to design and fabricate dental molds suitable for the production of elastic repositioning appliances and other dental appliances which require structure corresponding to a patient's oral soft tissue. Such dental molds should provide an oral soft tissue relief or mold replicating the oral soft tissues of the patient and a relief of the desired tooth configuration, whether the configuration be the patient's current tooth configuration or a new tooth configuration desired in orthodontic treatment. Such dental molds should be economical, and in particular should reduce the cost of materials, fabrication time and labor, and space required for storage of digital information. At least some of these objectives will be met by the present invention described hereinafter.

SUMMARY OF THE INVENTION

The present invention provides improved devices, systems and methods for producing dental molds, each having portions representing a patient's oral soft tissue and a desired tooth configuration. These molds are designed for use in the fabrication of appliances used in orthodontic treatment, particularly, elastic repositioning appliances. However, they may also be used in the fabrication of traditional appliances, such as retainers and positioners, used, for example in the final or finishing stages of an otherwise conventional treatment. The dental molds are comprised of a mold or relief of the patient's soft tissue, such as a palate, facial gingival tissue and/or lingual gingival tissue, and a separate or separable mold or relief of the patient's dental arch having teeth in a desired tooth configuration. Since, the tooth configuration will change as a patient progresses through orthodontic treatment, the relief of the dental arch will be fabricated separately from the relief of the oral soft tissue. Typically, the dental arch relief will be fabricated using rapid prototyping methods. The soft tissue relief may also be fabricated using rapid prototyping, however it may also be fabricated using traditional mold making methods, i.e., casting with plaster or other mold making materials. In either case, the resulting dental mold with be comprised of a "split-mold" having fixedly or removably joined arch and soft tissue reliefs.

When a patient is treated with elastic repositioning appliances, a series of such appliances are produced to gradually reposition the patient's teeth from an initial tooth configuration, through a series of intermediate tooth configurations, to a final or other targeted tooth configuration. To accomplish this, the patient's initial tooth arrangement and shape of the patient's dental arch are represented by a digital data set in a computerized model. The data set is then manipulated to reflect progressive tooth arrangements. For each arrangement, the data is used to guide computerized model fabrication systems, or rapid prototyping systems, to create a corresponding three-dimensional mold or relief. As described above, such systems may include stereolithography (SLA), laminate object manufacturing (LOM), and fused deposition modeling (FDM), to name a few. Due to the methodology of rapid prototyping systems, the resulting relief is typically comprised of fused layers of material, such as wax, plastic, flexible elastomers or paper.

At a given point in treatment, it may be necessary to produce an appliance which requires a mold having the oral soft tissue features of the patient. Since the majority of the soft tissue areas remain unchanged throughout orthodontic treatment, it is not necessary to use computerized models or rapid prototyping methods to generate a relief of the patient's soft tissue features. One may simply rely on the oral features of the patient prior to treatment or at the present time and traditional mold making methods using plaster casting, for example. This may eliminate the need to create and store a digital data set representing the soft tissue and, consequently, the added time and labor to manipulate the data sets to join the soft tissue with the dental arch in the computerized model. The resulting split or composite mold will then usually be comprised of a plaster relief of the patient's oral soft tissue and a fused layered relief of the patient's dental arch having a tooth arrangement reflecting a future stage in the orthodontic treatment protocol. The split mold may then be used to produce the desired appliance.

Split molds of the present invention may be comprised of a number of designs and may be fabricated using a number of methods. In a first aspect of the present invention, a split mold of an upper or lower jaw of a patient may be comprised of a dental arch relief and an oral soft tissue relief, formed separately from the dental arch relief, wherein the two reliefs are fixedly joined together to anatomically resemble the jaw of the patient. This may be achieved by a number of methods. In an exemplary method, an impression or other cavity mold of the patient's jaw is produced by traditional methods, such as pressing a dental molding material against the dental features to form depressions or contours corresponding to the teeth and oral features. An SLA model of the desired tooth arrangement (without the majority of the soft tissue features) is also generated to provide the dental arch relief. However, it may be appreciated that the dental arch relief may be fabricated by any known method. The dental arch relief is then positioned in the impression so that contours of the arch relief generally correspond to corresponding contours of the impression or cavity mold. Since the arch relief will likely resemble a future tooth arrangement, the contours of the arch relief may not exactly fit the contours of the impression. However, the differences may be overcome by the flexibility of the impression. With the dental arch relief inserted, the exposed remainder of the impression represents the soft tissue. A mold of the soft tissue may be produced by at least partially filling the remainder of the impression with molding material. Preferred molding materials include, but are not limited to, plaster, urethane, silicone, epoxy and wax. The molding material will flow to fill in exposed areas around the tooth members and will form a relief of the soft tissue. After the material has cured, the fixedly joined reliefs may be removed from the impression. The resulting split-mold may then be used to produce a dental appliance requiring the presence of teeth and soft tissue features.

In a second aspect of the present invention, a split or composite mold of an upper or lower jaw of a patient may be comprised of a dental arch relief and an oral soft tissue relief, formed separately from the dental arch relief, wherein the two reliefs are separably or removably joined together to anatomically resemble the jaw of the patient. In a preferred embodiment, the oral soft tissue relief may be comprised of a portion or portions of the patient's gingival anatomy with vacant space(s) in the area of the dental arch. For example, the oral soft tissue relief may be comprised of a mold of a palate and facial gingival tissue wherein a vacant arch shaped "cutout" exists between the palate and the facial gingiva. A dental arch relief having a first tooth configuration may then be inserted into the arch shaped cutout to fill the vacant space. In particular, the dental arch relief will have a bottom or base which is configured to mate with the cutout in the palate and facial mold, and the present invention includes systems which comprise a plurality of dental arch reliefs (usually having different tooth arrangements) which may be interchangeably mounted into the palate and facial mold. The result is a corporate structure which anatomically resembles the jaw of the patient having a first tooth configuration. The dental arch relief may then be removed and a different dental arch relief having a second tooth configuration may be inserted. The result would be a corporate structure which anatomically resembles the jaw of the patient having the second tooth configuration. This may be repeated with any number of dental arch reliefs. Thus, the soft tissue relief may remain constant or act as a "universal" soft tissue mold, while the dental arch reliefs may be interchangeable to represent different configurations. It may be appreciated that the soft tissue relief may simply comprise a portion of the soft tissue, such as the palate or a lingual gingival surface, which may join with the arch relief in at one or more specific locations. For example, the soft tissue relief may join or attach to the side of the arch relief so that the arch relief is not specifically inserted into the soft tissue relief.

The dental arch relief is typically generated by rapid prototyping methods, as described above, such as SLA, LOM, and FDM. Consequently, the relief is often comprised of fused layers of waxes, plastics, flexible elastomers or paper. In addition, the relief may be painted or coated to provide desired surface characteristics. Although the dental arch relief is primarily comprised of tooth members, the gingiva surrounding the tooth members may also be represented. This may be necessary because the gingiva in contact with or near the tooth members may vary with the tooth configurations. Therefore, it may not be feasible to include this in the soft tissue relief and may be provided by the dental arch relief.

The oral soft tissue relief is typically generated by traditional mold making methods. This may involve forming an impression of the patient's jaw using a suitable impression material, such as alginate or polyvinylsiloxane (PVS). Usually, this will include both the teeth and the oral soft tissues to ensure complete coverage. Plaster or other material may be poured into the impression to form a relief of the dental features. Upon removal of the mold from the impression, the mold may then be modified for use. The mold may be cut or trimmed to isolate a desired portion of the oral soft tissue relief. For example, the dental arch may be removed from the mold, leaving the relief of the palate and facial gingival surfaces intact. In this case, the mold may appear as an oral soft tissue relief having an arch-shaped hole or vacant space in place of the teeth. Thus, a dental arch relief, described above, may be inserted through the arch-shaped hole and held in place. The result may be a split-mold which anatomically resembles the jaw of the patient and may be used to produce a properly fitting appliance.

Similarly, other portions of the mold may be removed leaving portions of the soft tissue relief intact. For example, the lingual gingival surfaces of a lower jaw mold may be cut and isolated for use. In this case, the gingival surfaces or soft tissue relief may be joined with a dental arch relief by placing them in close proximity, snapping them together, bonding them together or joining them by any suitable method. Again, the result may be a split-mold which anatomically resembles portions of the jaw of the patient and may be used to produce a properly fitting appliance. For some appliances, this may be accomplished by heating a thermoformable polymer material and applying vacuum or pressure to form the polymer to the mold. An accessory, such as a lingual pad, may be formed in the appliance which contacts or interacts with the patient's lingual gingival surfaces.

The oral soft tissue relief may also be generated by rapid prototyping methods, as described above, such as SLA, LOM, and FDM. In this case, a digital data set may be created representing the oral soft tissue. The data set may be used to guide the computerized model fabrication systems to create a corresponding three-dimensional mold or relief. Since the data set may be modified prior to model fabrication, the resulting oral soft tissue relief may be generated in a usable form. Otherwise, the relief may be modified by manual methods so isolate the desired portion of the relief. In any case, the oral soft tissue relief may then be joined with a dental arch relief by placing them in close proximity, snapping them together, bonding them together or joining them by any suitable method. Again, the result may be a split-mold which anatomically resembles portions of the jaw of the patient and may be used to produce a properly fitting appliance. Although the reliefs may be comprised of the same material generated by the same methods, the advantages of the split-mold design are still available. The dental arch relief having a first tooth configuration may be removed and a dental arch relief having a second tooth configuration may be joined to the oral soft tissue relief. And, this may be repeated with third, fourth, fifth, and more tooth configurations. In addition, the digital data set may be used only once to fabricate a "universal" oral soft tissue relief. This may eliminate time and labor associated with manipulating the data sets to join the dental arch and the gingival tissues in the computer model at various times throughout the treatment. In addition, the digital data set representing the oral soft tissue may be deleted once the oral soft tissue relief is fabricated. This may eliminate the need for additional storage space.

Other objects and advantages of the present invention will become apparent from the detailed description to follow, together with the accompanying drawings.

DESCRIPTION OF THE SPECIFIC EMBODIMENTS

Split molds of the present invention may be comprised of a number of designs and may be fabricated using a number of methods. As previously described, a split mold of an upper or lower jaw of a patient may be comprised of a dental arch relief and an oral soft tissue relief, formed separately from the dental arch relief. The reliefs may be fixedly or removably joined together to anatomically resemble the jaw of the patient.

Figure 1:
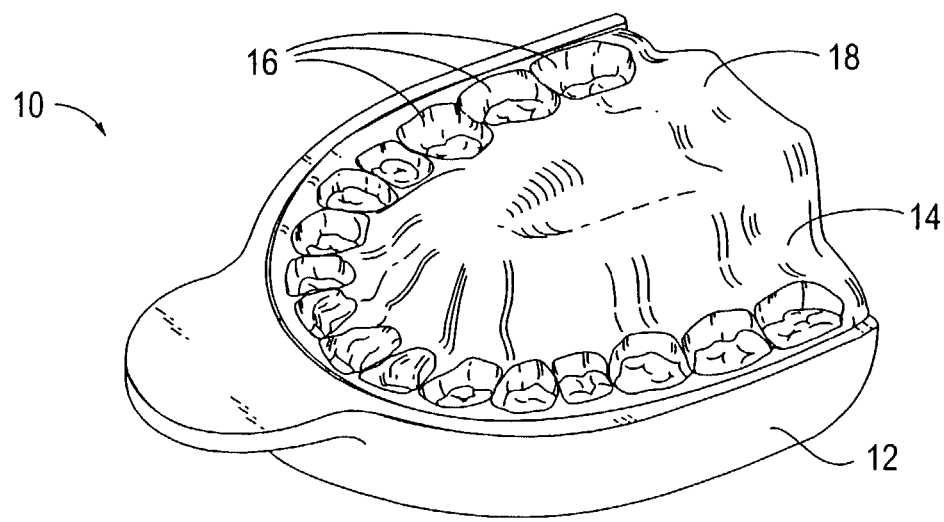
FIG. 1 is a perspective illustration of an dental impression made from a patient's jaw.
Figure 2:
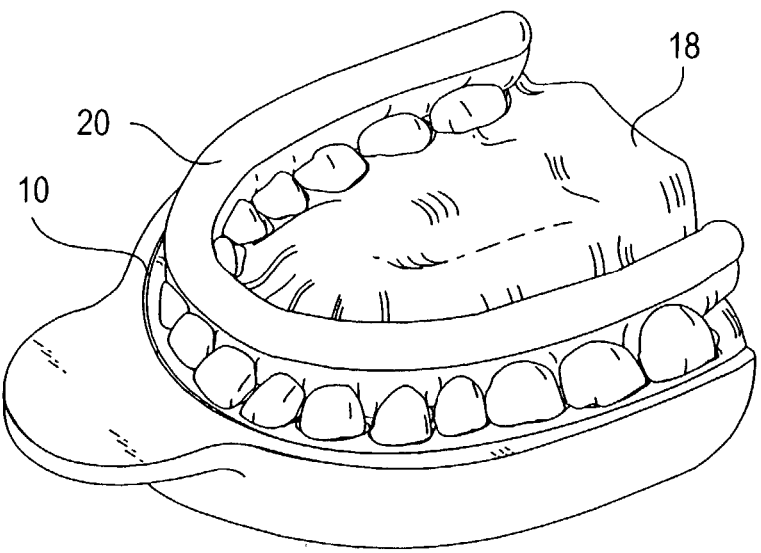
FIG. 2 illustrates the step of positioning a dental arch relief in the impression depicted in FIG. 1.
Figure 3:
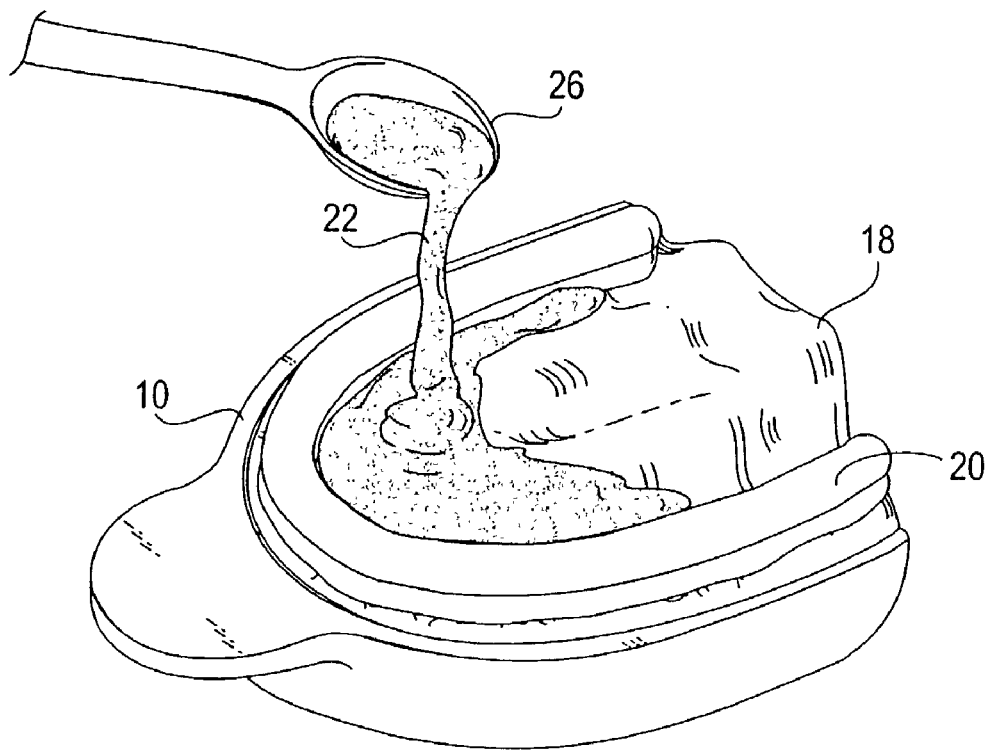
FIG. 3 illustrates the step of filling a remainder of the impression of FIG. 1 with a molding material.
Figure 4:
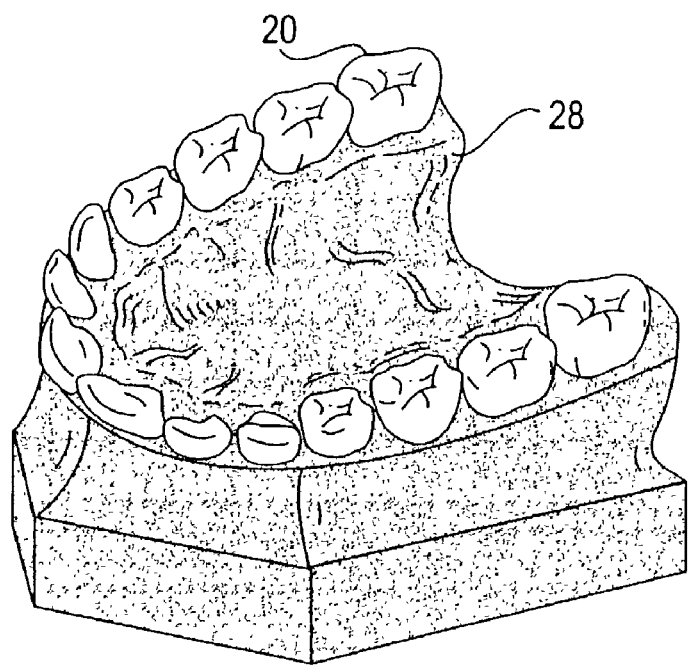
FIG. 4 is a perspective illustration of a split-mold formed by methods of the present invention illustrated in FIGS. 1–3.

In a first aspect of the present invention, the split mold may be produced wherein the dental arch relief and oral soft tissue relief are fixedly joined. Referring to FIG. 1, the a preferred method may begin by forming an impression 10 of the patient's jaw. A holder 12 may be filled with dental molding material 14, such as alginate, inserted in the patient's mouth and pressed against the patient's dental features. The resulting impression 10 may have depressions or contours in the material corresponding to the teeth 16 and oral features, such as the palate 18. As shown in FIG. 2, a dental arch relief 20, fabricated by any known method, particularly SLA, may then be positioned in the impression 10 so that contours of the arch relief generally correspond to contours of the impression. With the dental arch 20 inserted, the exposed remainder of the impression 10, such as the palate 18, represents the soft tissue. Referring to FIG. 3, the mold of the soft tissue may be produced by filling the remainder of the impression 10 with molding material 22. The molding material 22 is depicted flowing from a spoon 26 into the region of the palate 18. In this manner, the material 22 will flow around the dental arch relief 20 and will fill in exposed areas around the tooth members. After the material 22 has cured, the impression 10 may be removed. The result, as shown in FIG. 4, may be comprised of a dental arch relief 20 and an oral soft tissue relief 28 fixedly joined. In this case, the oral soft tissue relief 28 may comprise the entire surface area of the mold aside from the tooth members. This is possible due to the methodology of fabrication.

Figure 5A:
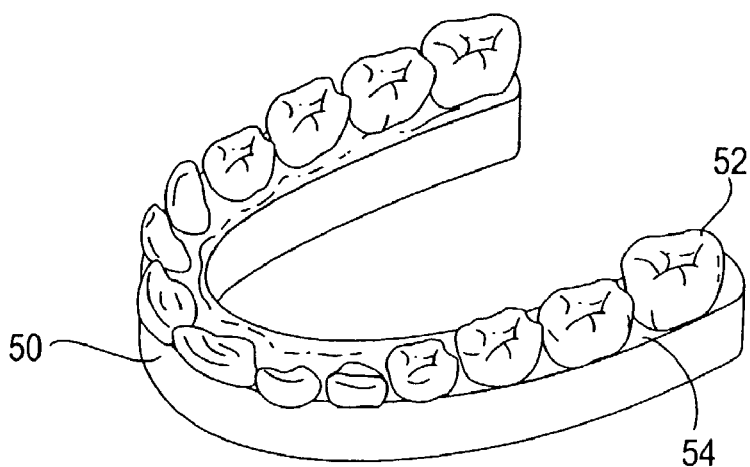
FIG. 5A depicts a dental arch relief of an upper jaw.
Figure 5B:
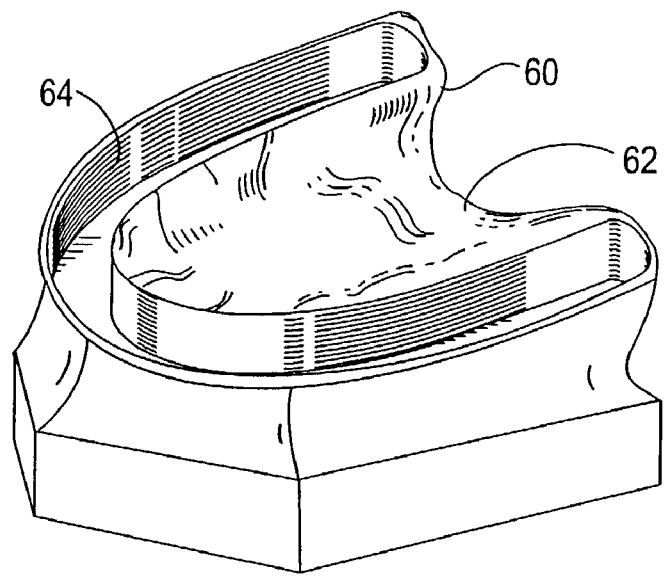
FIG. 5B depicts an oral soft tissue relief having a cutout in the area of the dental arch relief.
Figure 5C:
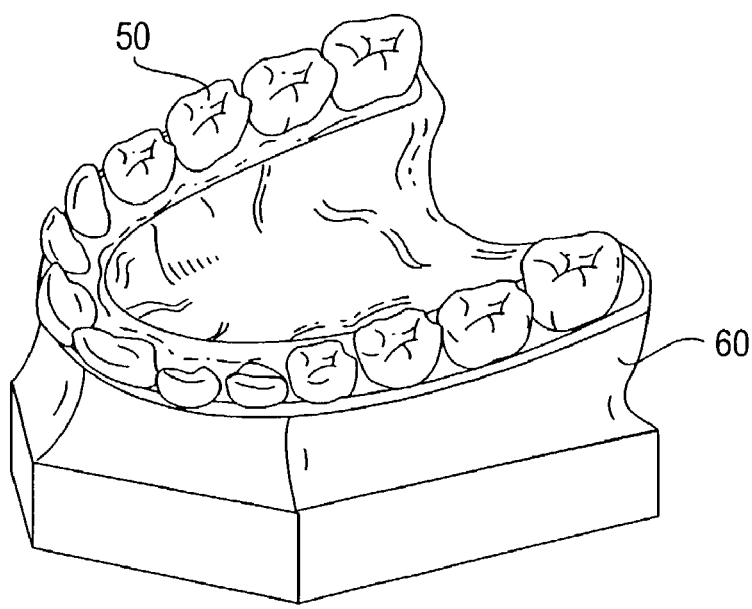
FIG. 5C is a perspective illustration of a split-mold formed by joining the reliefs depicted in FIGS. 5A–5B.

In a second aspect of the present invention, the split mold may be produced wherein the dental arch relief and oral soft tissue relief are removably joined. A preferred embodiment of such a system is illustrated in FIGS. 5A–C. FIG. 5A depicts a first dental arch relief 50 of an upper jaw having a first tooth configuration. In this case, the dental arch relief 50 may provide a mold of tooth members 52 and gingival tissue 54 surrounding the tooth members 52 along the arch. FIG. 5B depicts an oral soft tissue relief 60 of an upper jaw, including a palate 62. As shown, an arch-shaped cutout 64 or vacant space may exist surrounding the palate 62. The dental arch relief 50 may then be inserted into the cutout 64 to fill the vacant space. The resulting split-mold, shown in FIG. 5C, comprises a dental arch relief 50 and oral soft tissue relief 60 removably joined to anatomically resemble the upper jaw of the patient having the first tooth configuration. The arch relief 50 may then be removed and a second dental arch relief having a second tooth configuration, similar to the relief 50 depicted in FIG. 5A with a slightly differing tooth arrangement, may be inserted into the cutout 64. The resulting split-mold may anatomically resemble the upper jaw of the patient having the second tooth configuration. This may be repeated with any number of dental arch reliefs.

Figure 6A:
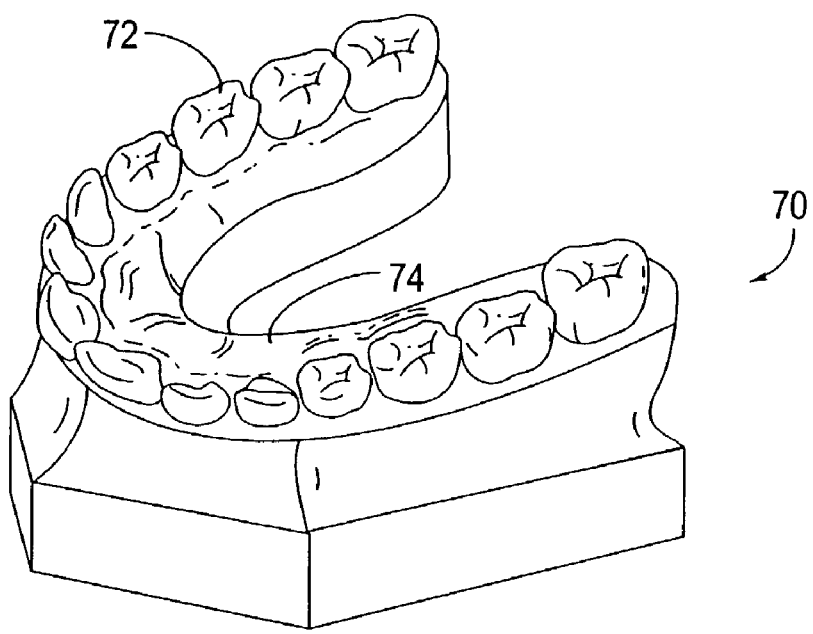
FIG. 6A depicts a mold of a lower jaw of a patient.
Figure 6B:
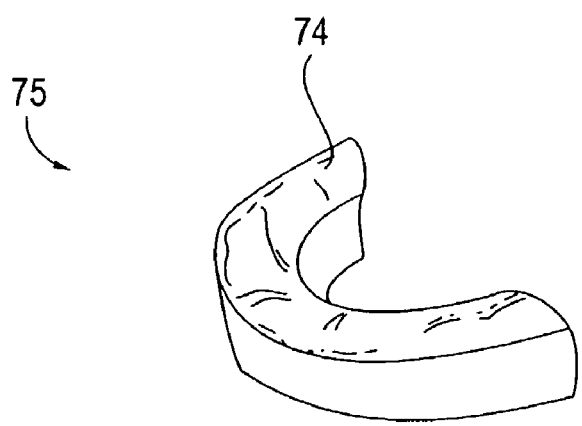
FIG. 6B depicts an oral soft tissue relief, representing the portions of the lingual gingival surfaces of the patient's lower jaw, which has been cut and removed from the mold depicted in FIG. 6A.

The above described system may be produced using a number of methods. In a preferred method, the oral soft tissue relief is generated by traditional mold making methods. This may involve forming an impression of the patient's jaw using a suitable impression material, such as alginate or polyvinylsiloxane (PVS). Plaster or other material may be poured into the impression to form a relief of the dental features. Upon 10 removal from the impression, a three-dimensional mold results. An example of such a mold 70 of a lower jaw of a patient is depicted in FIG. 6A. As shown, the mold 70 may have features representing both tooth members 72 and lingual gingival tissue 74, for example. The mold 70 may be cut or trimmed to isolate the lingual gingival tissue 74. The result, depicted in FIG. 6B, is an oral soft tissue relief 75 of the lingual gingival tissue.

Figure 7:
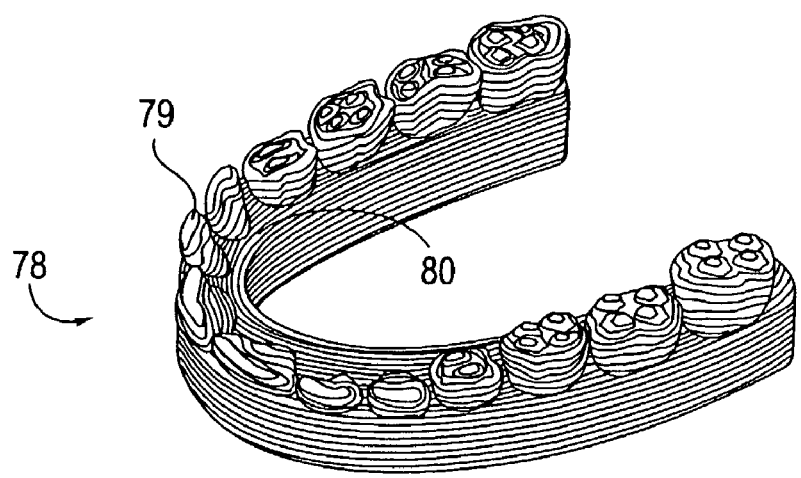
FIG. 7 depicts an dental arch relief of a lower jaw.
Figure 8:
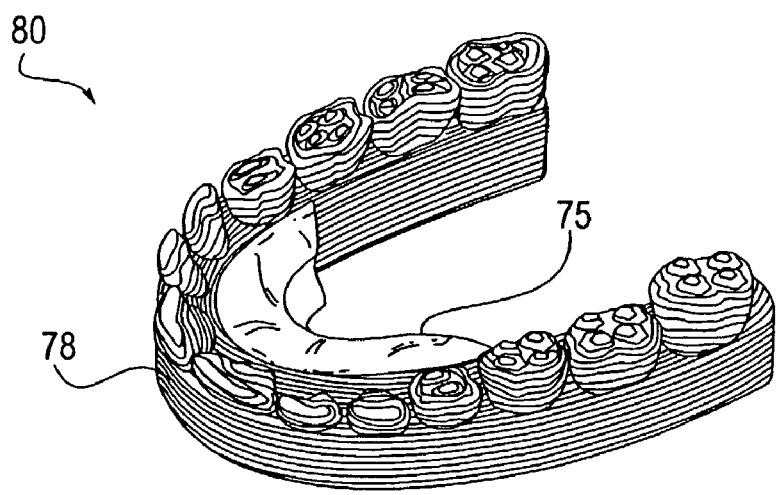
FIG. 8 is a perspective illustration of a split-mold formed by methods of the present invention illustrated in FIGS. 6A, 6B, and 7.

A dental arch relief may be generated by any method, but will typically be generated by rapid prototyping methods, such as SLA, LOM, and FDM, to name a few. As used herein, "rapid prototyping" will refer to any computer-controlled method for directly fabricating the relief structure from a structuring material. SLA, LOM, and FDM, are presently the best known of such techniques, but other and future techniques will also be useful. In these cases, the dental arch relief is comprised of fused layers of waxes, plastics, flexible elastomers or paper. Such a dental arch relief 78 is depicted in FIG. 7 and represents a lower jaw having a first tooth configuration. Again, the dental arch relief 78 may provide a mold of tooth members 79 and gingival tissue 80 surrounding the tooth members 79 along the arch. Horizontal lines throughout the relief 78 illustrate such layers. Referring to FIG. 8, the dental arch relief 78 and the oral soft tissue relief 75 may be joined to form a split-mold 80 which resembles portions of the lower jaw of the patient. Such joining may be removable or fixed.

Removably joining the reliefs may involve a number of methods to hold the reliefs in place. For instance, the reliefs may be interlocking or snap together to form a joined mold. Or, the reliefs may be attached by any type of fastener, screw, bolt, hook, clasp, hoop-and-loop fasteners (e.g., those available under the tradename Velcro®), or similar device. Likewise, the reliefs may be removably bonded by tape, adhesive, or similar material. And finally, the reliefs may be press-fit and held by wedging or friction. It may be appreciated that a combination of any of these methods may be used or similar methods that may provide the same function. Further, it may be appreciated that the reliefs may be joined simply by placing the reliefs in close proximity to each other. A soft tissue relief may be positioned in a desired location near a portion or portions of the dental relief, and the reliefs may be used together in the production of a dental appliance. Also, any of the removably joined reliefs may become permanently joined or fixedly attached by the addition of a material, agent or device which will fixedly bond the relief materials, such as an adhesive.

The resulting split-mold resembles portions of the lower jaw of the patient and may be used to produce a properly fitting appliance. For some appliances, this may be accomplished by heating a thermoformable polymer material and applying vacuum or pressure to form the polymer to the mold. In this case, a lingual pad or similar accessory may be formed in the appliance which contacts or interacts with the patient's lingual gingival surfaces of the lower jaw.

In addition, the oral soft tissue relief 75 may be produced by any other method, including rapid prototyping methods. FIGS. 6A, 6B, 7 and 8 also illustrate such a method but may be further visualized by adding horizontal lines throughout the mold 70 and the oral soft tissue relief 75 to illustrate a layered material composition. As previously mentioned, the advantages of the split-mold design are still available when the reliefs are be comprised of the same material generated by the same methods. The dental arch relief having a first tooth configuration may be removed and a dental arch relief having a second tooth configuration may be joined to the oral soft tissue relief. And, this may be repeated with third, fourth, fifth, and more tooth configurations. In addition, the digital data set may be used only once to fabricate a "universal" oral soft tissue relief. This may eliminate time and labor associated with manipulating the data sets to join the dental arch and the gingival tissues in the computer model at various times throughout the treatment. In addition, the digital data set representing the oral soft tissue may be deleted once the oral soft tissue relief is fabricated. This may eliminate the need for additional storage space.

Although the foregoing invention has been described in some detail by way of illustration and example, for purposes of clarity of understanding, it will be obvious that various alternatives, modifications and equivalents may be used and the above description should not be taken as limiting in scope of the invention which is defined by the appended claims.

What is claimed is:

1. A dental mold of a jaw of a patient comprising:
   a dental arch relief comprising a single unitary mold having shapes representing tooth members of the patient in a fixed tooth arrangement; and
   an oral soft tissue relief representing oral soft tissue of the patient, wherein the oral soft tissue relief is formed separately from the dental arch relief,
   wherein the arch relief and the tissue relief are joined.

2. A dental mold of claim 1, wherein the oral soft tissue comprises at least one of a palate, a facial gingival tissue, and a lingual gingival tissue.

3. A dental mold of claim 1, wherein the arch relief and the tissue relief are separably joined.

4. A dental mold of claim 1, wherein the arch relief and the tissue relief are fixedly joined.

5. A dental mold of claim 1, wherein the dental arch relief comprises a material selected from the group consisting of fused layers of waxes, plastics, flexible elastomers, and paper.

6. A dental mold of claim 1, wherein the oral soft tissue relief comprises a material selected from the group consisting of plaster, fused layers of waxes, plastics, flexible elastomers, and paper.

7. A method of making a dental mold of a jaw of a patient comprising:
   providing a dental arch relief comprising a single unitary mold having shapes representing tooth members of the patient in a fixed tooth arrangement;
   providing an oral soft tissue relief representing oral soft tissue of the patient; and
   joining the arch relief and the soft tissue relief to form a mold of the jaw.

8. A method of claim 7, wherein the dental arch further comprises gingiva surrounding the tooth members.

9. A method of claim 7, wherein the oral soft tissue comprises a palate, a facial gingival surface and/or a lingual gingival surface.

10. A method of claim 7, wherein joining comprises inserting the dental arch relief into the oral soft tissue relief so that together the reliefs anatomically resemble the jaw of the patient.

11. A method of claim 10, wherein inserting comprises separably attaching the dental arch relief to the oral soft tissue relief.

12. A method of claim 10, wherein inserting comprises fixedly attaching the dental arch relief to the oral soft tissue relief.

* * * * *